United States Patent [19]

Kensicher et al.

[11] Patent Number: 5,783,533
[45] Date of Patent: Jul. 21, 1998

[54] AMPHOTERIC AGENTS AS MODIFIERS OF LAMELLAR PHASES OF DETERGENTS OR LIQUID OR PASTY COSMETIC COMPOSITIONS

[75] Inventors: Yves Kensicher, Lozanne; Jean-Marc Suau, Lucenay, both of France

[73] Assignee: Coatex S.A., Genay Cedex, France

[21] Appl. No.: 620,360

[22] Filed: Mar. 22, 1996

[30] Foreign Application Priority Data

Mar. 23, 1995 [FR] France ................ 95 03646

[51] Int. Cl.$^6$ ................ C11D 3/37; A61K 7/06
[52] U.S. Cl. ................ 510/119; 510/108; 510/123; 510/124; 510/405; 510/475; 510/476; 424/70.1; 514/844
[58] Field of Search ................ 510/475, 476, 510/119, 123, 108, 124, 405; 424/70.1; 514/844

[56] References Cited

U.S. PATENT DOCUMENTS

| | | | |
|---|---|---|---|
| 4,431,548 | 2/1984 | Lipowski et al. | 210/732 |
| 4,983,383 | 1/1991 | Maksimoski et al. | 424/70 |
| 5,275,809 | 1/1994 | Chen et al. | 424/70 |
| 5,296,218 | 3/1994 | Chen et al. | 424/70 |
| 5,413,731 | 5/1995 | Adler et al. | 510/230 |

FOREIGN PATENT DOCUMENTS

| | | |
|---|---|---|
| 0 112 592 | 7/1984 | European Pat. Off. |
| 0 346 995 | 12/1989 | European Pat. Off. |
| 0 458 599 | 11/1991 | European Pat. Off. |
| 0 522 756 | 1/1993 | European Pat. Off. |
| 2 470 596 | 6/1981 | France. |
| 2 104 091 | 3/1983 | United Kingdom. |
| WO 91/06623 | 5/1991 | WIPO. |
| 9109067 | 6/1991 | WIPO. |
| WO 92/04437 | 3/1992 | WIPO. |
| WO 92/17153 | 10/1992 | WIPO. |

*Primary Examiner*—Paul Lieberman
*Assistant Examiner*—Lorna M. Douyon
*Attorney, Agent, or Firm*—Oblon, Spivak, McClelland, Maier & Neustadt, P.C.

[57] ABSTRACT

Amphoteric copolymers of general formula:

$$(X)_a—(Y)_b—(Z)_c$$

in which
  X represents a monomer type with anionic charge;
  Y represents a monomer type with nonionic character;
  Z represents a monomer type with cationic charge;
  a is the weight % based on the total weight of monomers of X, and is between 95 and 15;
  b is the weight % based on the total weight of monomers of Y, and is between 0 and 65;
  c is the weight % based on the total weight of monomers of Z, and is between 5 and 60 as rheological modifiers of lamellar phases of detergent or cosmetic (liquid or pasty) compositions are disclosed. Liquid washing detergent and liquid shampoos containing the amphoteric copolymers are also disclosed.

19 Claims, No Drawings

AMPHOTERIC AGENTS AS MODIFIERS OF LAMELLAR PHASES OF DETERGENTS OR LIQUID OR PASTY COSMETIC COMPOSITIONS

BACKGROUND OF THE INVENTION

1. Field of the Invention

The present invention relates to methods for modifying the rheological properties of aqueous compositions containing lamellar phases by the inclusion of a specified modifying agent in the composition. The present invention further relates to aqueous compositions, in particular detergents and liquid or creamy cosmetics, which contain such a modifying agent.

Thus the present invention relates to the use of copolymers comprising at least two types of monomeric units, with the first type being composed of one or more ethylenic monomer units with an anionic charge, the second type being composed of one or more ethylenic monomer units with a cationic charge, with at least one of these cationic charged monomers having a surface-active structure, and optionally comprising a third type which is composed of one or more nonionic ethylenic monomer units as a rheological modifying, amphoteric agent of lamellar phases in an aqueous phase.

The present invention also relates the use of such rheological modifying copolymers for the thickening or the fluidification of detergent or cosmetic compositions, liquid or pasty, what ever the ionicity of the ingredients forming the compositions, that is to say anionic, cationic, or non-ionic. The present invention also relates to the use of such copolymer agents to improve the compatibility of such anionic and cationic mixtures.

2. Discussion of the Background

Nowadays, for reasons of ease of use, consumers use more and more liquid detergent compositions. Those compositions, in order to be efficient, contain anionic and non-ionic surface-active structures that form micelles in aqueous phases and arrange themselves as more or less concentrated lamellae when "builders" of the borax, citrate, sodium formate or even weak acid salt types are incorporated in more or less large quantities in the composition. It is then commonly said that it is a matter of lamellar anionic phases.

The same applies when such compositions contain cationic and non-anionic surface-active structures. The use in much larger or smaller quantities of the same "builders" leads to the formation of more or less concentrated cationic lamellar phases.

In fact, the presence of such lamellar phases, either anionic or cationic, conditions the viscosity as well as the stability of the liquid detergent composition, just as the simultaneous presence of anionic and cationic lamellar phases when, for example, it is wished to propose to the consumers a single commercial product having an anionic liquid detergent composition associated with a cationic softener or again, for example, an anionic shampooing composition associated with a cationic or amphoteric hair conditioner.

If those lamellar phases are to concentrated, they then occupy an important fraction of the liquid's volume thus highly increasing the viscosity of the liquid formulation as well as the flocculation of the micelles leading potentially to a non pourability of the composition.

In the opposite manner, if those lamellar phases are too weakly concentrated, they then have a tendency to sediment resulting in a loss of stability for the composition. A similar type of problem is also seen in cosmetic formulation of the shampoo type.

Until now, different solutions have been proposed to solve the problem of viscosity and stability of the final composition.

Thus, European Patent Application EP 0 346 995 proposes the use of a deflocculent polymer containing a hydrophilic skeleton and one or several hydrophobic lateral chains. However, this approach does not result in compatibility of the anionic lamellar phases with cationic lamellar phases when those two are jointly present in the composition.

In the same manner, U.S. Pat. No. 5,275,809 describes the use of dimethyldiallyl ammonium chloride based terpolymers in anionic formulations of shampoos. But here again, this type of copolymer doesn't result in compatibility with any kind of anionic or cationic formulation.

Another solution is proposed in European Patent Application EP 0 564 250, which describes the use of peroxyacids that have a special solubility in water.

Thus, there remains a need for methods and agents useful for modifying the rheological properties of aqueous compositions containing lamellar phases. There also remains a need for methods and agents useful for stabilizing aqueous compositions containing both anionic and cationic lamellar phases.

SUMMARY OF THE INVENTION

Accordingly, it is one object of the present invention to provide a novel method for improving the rheological properties of aqueous compositions which contain lamellar phases.

It is another object of the present invention to provide a novel method for improving the stability of aqueous compositions which contain both anionic and cation lamellar phases.

It is another object of the present invention to provide novel copolymers useful for carrying out such methods.

It is another object of the present invention to provide novel compositions, including detergents and liquid or pasty cosmetics, which contain such a copolymer.

These and other objects, which will become apparent during the following detailed description, have been achieved by the inventors' discovery that inclusion of a copolymer comprising monomer units derived from at least two monomer types with the first type being composed of one or more ethylenically unsaturated monomers with an anionic charge, the second type being composed of one or more ethylenically unsaturated monomers with a cationic charge, with at least one of these cationic charged monomers having a surface-active structure, that is to say containing one or more side chains composed of alkyl, aryl, alkylaryl or arylalkyl groups having at least 8 carbon atoms, and optionally a third type of monomer which is composed of one or more nonionic monomers in an aqueous composition containing a lamellar phase, can be used in a surprising manner, by the ionic interactions between the copolymer and the different lamellar phases in the aqueous phase, to modify the stability and the viscosity of the liquid or pasty, detergents or cosmetics compositions, such as for example shampoos. The inventors have also discovered that such copolymers can be used to improve the compatibility of the diverse anionic and cationic lamellar phases when the liquid or pasty compositions contain both anionic and cationic phases.

DETAILED DESCRIPTION OF THE PREFERRED EMBODIMENTS

Thus, in a first embodiment, the present invention provides a method for modifying the rheology of the lamellar phases in an aqueous phase in detergent or cosmetic liquid or pasty compositions such as shampoos, by including in such a composition a copolymer having the general formula:

$$(X)_a—(Y)_b—(Z)_c$$

in which:

- each X independently represents a monomer unit derived from a monomer of the first type having an anionic charge and composed of one or more ethylenically unsaturated monomers with anionic charge;
- each Y independently represents a monomer unit derived from a monomer of the third type having a nonionic character and composed of one or more nonionic monomers;
- each Z independently represents a monomer unit derived from a monomer of the second type having a cationic charge and composed of one or more ethylenically unsaturated monomers with cationic charge with one at least of those monomers having a surface-active structure, that is to say, containing one or more lateral chains composed of alkyl, aryl, alkylaryl or arylalkyl groups having at least 8 carbon atoms;
- a is the weight percentage of, based on the total weight of all monomers and, is from 95 to 15, preferably 80 to 25, limits included;
- b is the weight percentage of, based on the total weight of all monomers and is from 0 to 65, preferably 20 to 50, limits included;
- c is the weight percentage of, based on the total weight of all monomers, and is from 5 to 60, and particularly from 10 to 35, limits included.

In another embodiment, the present invention provides a method for the thickening or the fluidification of detergent or cosmetic (liquid or pasty) compositions and a method for improving the compatibility of the different phases of detergent or cosmetic compositions by including such a copolymer in the composition.

In another embodiment, the present invention provides detergent or cosmetic, liquid or pasty, compositions, such as shampoos for example, which contain the present rheological modifying copolymer.

Thus, the methods according to the present invention differ from the prior art description of the use of deflocculent polymers comprising a hydrophilic skeleton and one or more hydrophobic lateral chains, by the fact that the rheological modifying agent always comprises at least two types of monomeric units with the first type being derived from one or more ethylenically unsaturated monomers with an anionic charge, the second type being derived from one or more ethylenically unsaturated monomers with a cationic charge, with at least one of those cationic charged monomers having a surface-active structure, that is to say containing one or more side chains composed of alkyl, aryl, alkylaryl or arylalkyl groups possessing at least 8 carbon atoms, and optionally a third type of monomeric unit being derived from one or several nonionic monomers. In a preferred embodiment, the present copolymer has the general formula (I):

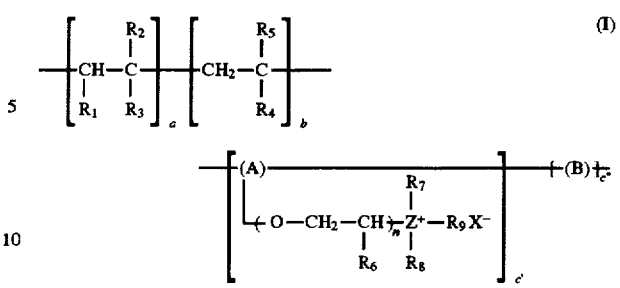

in which:

for the anionic type monomeric unit:
- $R_1$ is H or COOH,
- $R_2$ is H or $CH_3$,
- $R_3$ is a group containing at least one acidic function which may be totally or partially neutralized, for example COOH or COOM, where M may be Na, K, or $NH_4$, and
- a is the weight percentage of the anionic type monomer units, based on the total weight of all monomers, and is, limits included, between 95 and 15, preferably 80 to 25;

for the nonionic type monomeric unit:
- $R_4$ is

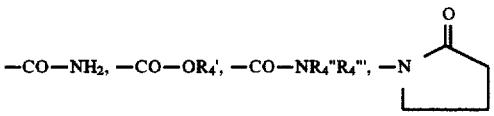

in which
- $R_4'$ is an alkyl or alkoxy radical having 1 to 4 carbon atoms,
- $R_4''$ is H or an alkyl radical having 1 to 4 carbon atoms,
- $R_4'''$ is an alkyl radical having 1 to 4 carbon atoms,
- $R_5$ is H or $CH_3$, and
- b is the weight percentage of the nonionic type monomeric unit, based on the total weight of all monomers, and is, limits included, between 0 and 65, preferably 20 to 50;

for the cationic type monomeric unit:
- A is a unit derived from a polymerizable ethylenically unsaturated radical selected from the group consisting of acrylic, methacrylic, maleic, itaconic, crotonic and vinylphthalic esters; maleic, itaconic, vinylphthalic hemiesters, an unsaturated urethane, such as for example acrylurethane, methacrylurethane, α,α-dimethyl-m-isopropenyl benzylurethane, allylurethane, allylic ethers, substituted or unsubstituted acrylamide, substituted or unsubstituted methacrylamides, and vinylic groups.
- $R_6$ is H or $CH_3$,
- n=2 to 30,
- $R_7$ is an alkyl group having 1 to 4 carbon atoms,
- Z is N or S,
- X is a sulfate or halogen counter-ion, and when Z is N:
  - $R_8$ is an alkyl chain having 8 to 22 carbon atoms or a linking group to another polymeric claim of formula (I) having the following formula:

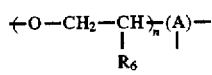

with n=2 to 30, where A has the same meaning as above and the two bonds from A are connected to two monomer units in another polymer chain of formula (I), and $R_9$ is an alkyl chain having 8 to 22 carbon atoms and when Z is S:

$R_8$ doesn't exist, $R_9$ is an alkyl chain having 8 to 22 carbon atoms, and c' is the weight percentage, based on the total weight of all monomers, of the cationic charged monomer having a surface-active structure, and is, limits included, between 5 and 60, and preferentially between 10 and 35 with c'+c"=c, c representing the weight percentage, based on the total weight of all monomers, of all the cationic monomers and varying between 5 and 60 and preferentially between 10 and 35, limits included;

B is a cationic monomeric unit which does not contain a surface-active structure and is derived from a monomer selected from the group consisting of trimethylaminoethyl acrylate chloride, trimethylaminoethyl methacrylate chloride, trimethylaminoethyl acrylate sulfate, trimethylaminoethyl methacrylate sulfate, trimethylaminopropyl acrylamide chloride, trimethylaminopropyl methacrylamide chloride, trimethylaminopropyl acrylamide sulfate, and trimethylaminopropyl methacrylamide sulfate, and c" is the weight percentage, based on the total weight of all monomers, of the cationic monomer which does not contain a surface-active structure, and is, limits included, between 0 and 55, preferably between 1 and 55, with c'+c"=c, c representing the weight percentage, based on the total weight of all monomers, of all the cationic charged monomers and varying between 5 and 60, and particularly between 10 and 35, limits included.

Specific examples of the trivalent group A in formula (I) include:

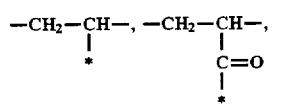

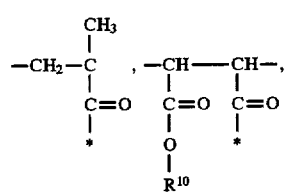

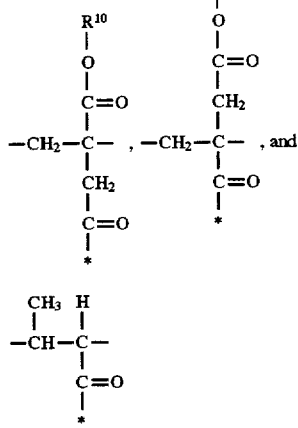

where the bonds marked with an * are the bonds linking A to the surface-active side chain group, and $R^{10}$ is a $C_{1-4}$ alkyl group or H.

The present copolymers may be prepared according to the conventional synthetic processes, including radical copolymerization solution processes, direct or inverse emulsion polymerization, suspension or precipitation processes, with initiators and appropriate regulators, in aqueous, alcoholic, aqueous-alcoholic, aromatic, aliphatic medium, or in an halogenated solvent, by polymerizing at least two monomeric types defined above.

Thus, the copolymerization media can be water, methanol, propanol, isopropanol, butanols or also dimethylformamide, dimethylsulfoxide, tetrahydrofuran, acetone, methylethylketone, ethyl acetate, butyl acetate, hexane, heptane, benzene, toluene, ethylbenzyl, xylene, halogenated solvents such as carbon tetrachloride, chloroform, dichloromethane, monopropyleneglycol, and diethyleneglycol ethers.

Copolymers to be used in the application, according to the invention, of fluidification of liquid detergent compositions or liquid or pasty cosmetic compositions are usually those having a specific viscosity, η, between 0.3 and 3.0 and preferably between 0.4 and 2.0.

Also, copolymers to be used in the application, according to the invention, of thickening liquid detergent compositions or liquid or pasty cosmetic compositions are usually those having a specific viscosity, η, greater than 3.0 and preferably greater than 10.

The specific viscosity of the chosen copolymers, which is symbolized by the symbol η, is determined according to the following procedure.

First, a solution of copolymer is prepared in the form of a sodium salt by dissolving 50 g of dry copolymer in a liter of a distilled water solution containing 60 g of sodium chloride. Then, one measures, with a capillary viscometer placed in a bath maintained at 25° C. by a thermostat, the flow time of a given volume of the above-cited solution containing the alkaline copolymer, as well as the flow time of the same volume of an aqueous solution of sodium chloride lacking the copolymer. It is then possible to define the specific viscosity η using the following equation:

$$\eta = \frac{t_{copolymer} - t_{NaCl}}{t_{NaCl}}$$

where:

$t_{copolymer}$=the flow time of the copolymer solution; and
$t_{NaCl}$=the flow time of the NaCl solution.

The capillary tube is usually chosen so that the flow time for the NaCl solution without the copolymer is about 90 to 100 seconds, which then gives values of specific gravity of a very good accuracy.

Right at the end of the polymerization, the acidic copolymers in aqueous solution are collected and according to the invention can be implemented in this form.

Then the chosen copolymers in aqueous solution are totally or partially neutralized with a neutralization agent containing a monovalent function such as the alkaline cations. Suitable neutralizing agents include NaOH, KOH, etc.

Practically, the liquid or heterogeneous phase obtained from the copolymerization and containing the chosen acidic copolymer can be used as its neutralized form as a rheological modifier, but it can also be dried by any known means in order to remove the liquid phase and isolate the copolymer as a fine powder that can be used in this other form.

In a broader perspective, the rheological modifier agent of the present invention can be included in the preparation of a detergent or cosmetic, liquid or pasty composition, by a method involving the following steps:

(a) preparing, with rapid agitation, but avoiding making too many bubbles, the anionic or cationic lamellar phase by introduction, according to the nature of the lamellar phase, of anionic, cationic and/or non-ionic surface-active compounds in water, eventually alkalinized, followed by an optional addition of other additives, such as for example builders, propylene glycol, optical brighteners, coloring agents and others;

(b) adding continuously to the lamellar phase thus prepared, at least 0.25 dry weight %, preferably 0.25 to 5 dry weight %, based on the total weight of the lamellar phase, of the rheological modifying copolymer of the present invention; and (c) in the case of the preparation of a stable and homogenous mixture of cationic and anionic phases, one proceeds to the mixture of the phases prepared according to step (a) and then adds at least 0.25 dry weight %, preferably 0.25 to 5 dry weight %, based on the total weight of the mixture, of the copolymer of the present invention.

In a general manner, the anionic surface-active compounds used in the preparation of the anionic lamellar phase include alkyl-benzene sulfonates, for example, including tetrapropylenebenzene sulfonate, the $C_{8-18}$ alkanesulfonates, the $C_{8-18}$ alkylsulfates, the $C_{8-18}$ alkylethersulfates, and others.

In the same manner, in the preparation of the cationic lamellar phases, the cationic surface-active compounds are among others and for example imidazole salts, $C_{8-18}$ dialkyldimethylammonium chlorides, and $C_{8-18}$ alkyldimethylbenzyl ammonium chlorides.

Moreover for any type of formulation, the nonionic surface-active compounds are chosen for example among ethoxylates of $C_{8-22}$ fatty alcohols, oxo alcohols, $C_{8-18}$ alkylphenols as well as the $C_{8-18}$ alkyl polyglycol, $C_{8-18}$ alkylphenol polyglycol ethers or also the alkanolamides of fatty acids or others.

In a similar manner, the different additives used in the preparation of the lamellar phase are for example builders, propylene glycol, optical brighteners, coloring agents or others.

As soon as the quantity of the rheological modifier of the present invention, added to the lamellar phase, achieves the desired fluidification or thickening and stability, one obtains the detergent or cosmetic composition, liquid or pasty, according to the present invention.

Other features of the invention will become apparent in the course of the following descriptions of exemplary embodiments which are given for illustration of the invention and are not intended to the be limiting thereof.

EXAMPLES

Example 1

This example concerns the fluidification of an anionic liquid detergent composition by the use of amphoteric rheological modifiers of lamellar phases, according to the present invention.

In order to achieve this goal, for each of the trials of the example, one prepares the anionic liquid detergent composition by adding into a 5 liter beaker, fitted with an agitator blade of 70 mm diameter, 1400 g of water and 10.6 g of sodium hydroxide. After complete dissolution of the sodium hydroxide one adds under agitation 25.7 g of monoethanolamine, 257.3 g of sodium dodecylbenzene sulfonate and 695.9 g of 9 times ethoxylated nonylphenol respectively, before adding last and simultaneously 30.5 g sodium carbonate and 144.1 g trisodium citrate.

The agitation is continued for 5 minutes before the required quantity of amphoteric agent corresponding to 0.56 dry weight % of amphoteric agent based on the total weight of the formulation is added.

After 20 minutes of agitation of the composition thus obtained, one measures the viscosities of the different trials at 10, 20 and 100 rpm and 25° C. with a Brookfield viscometer of the RVT type equipped with the adequate spindle. The different trials are done with the following copolymer amphoteric rheological modifiers of lamellar phases:

Trial No. 1

This trial is the control in which no copolymer amphoteric agent is introduced.

Trial No. 2

This trial illustrates the invention and uses an amphoteric rheological modifier of lamellar phases which is prepared from the following monomer mixture:

47.4 weight % of acrylic acid for the anionic charged monomer 41.8 weight % of acrylamide for the monomer with a nonionic character and 10.8 weight % of a cationic charged monomer of formula:

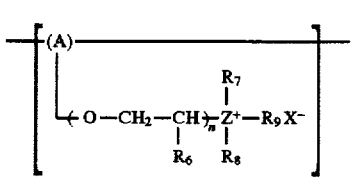

in which (A) is the residue of an unsaturated radically polymerizable and polymerized monomer, obtained from the condensation reaction of the ethylene glycol methacrylate with diisocyanate toluene having the formula:

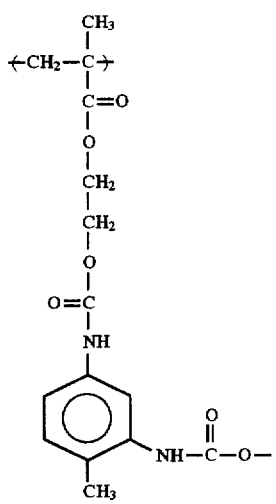

R$_6$ is H
n=5−m
R$_7$ is CH$_3$
R$_8$ is the radical —(A)—(O)—CH$_2$—CH$_2$—)$_m$ with m+n=5
R$_9$ is an alkyl radical with 12 carbon atoms
Z=N
X=SO$_4$CH$_3$
and which specific viscosity is 0.56.

Trial No. 3

This trial illustrates the invention and uses an amphoteric rheological modifier of lamellar phases which monomeric composition is identical to the agent of trial No. 2 but which specific viscosity is 0.8.

Trial No. 4

This trial illustrates the invention and uses an amphoteric rheological modifier of lamellar phases which monomeric composition is identical to the agent of trial No. 2 but which specific viscosity is 2.03.

Trial No. 5

This trial illustrates the invention and uses an amphoteric rheological modifier of lamellar phases which monomeric composition is:

41.9 weight % of an equimolar mixture of acrylic acid and methacrylic acid for the anionic charged monomer 41.0 weight % of acrylamide for the monomer with non-ionic character 10.6 weight % of cationic charged monomer of same formula as the one of trial No. 2 with cationic charge 6.5 weight % of trimethylaminoethyl methacrylate ammonium chloride as a second monomer with cationic charge, and which specific viscosity is 0.67.

Trial No. 6

This trial illustrates the invention and uses an amphoteric rheological modifier of lamellar phases which monomeric composition is:

36.6 weight % of acrylic acid for the anionic charged monomer 40.2 weight % of acrylamide for the monomer with nonionic character 10.4 weight % of cationic charged monomer of same formula as the one of trial No. 2 with cationic charge 12.8 weight % of trimethylaminoethyl methacrylate ammonium chloride as a second monomer with cationic charge, and which specific viscosity is 0.56.

Trial No. 7

This trial illustrates the invention and uses an amphoteric rheological modifier of lamellar phases which monomeric composition is:

47.4 weight % of acrylic acid for the anionic charged monomer 41.8 weight % of n-vinyl pyrrolidone for the monomer with nonionic character, and 10.8 weight % of cationic charged monomer of same formula as the one of trial No. 2 with cationic charge, and which specific viscosity is 0.78.

Trial No. 8

This trial illustrates the invention and uses an amphoteric rheological modifier of lamellar phases which monomeric composition is:

89.2 weight % of acrylic acid for the anionic charged monomer 10.8 weight % of cationic charged monomer of same formula as the one of trial No. 2 with cationic charge and which specific viscosity is 0.46.

Trial No. 9

This trial illustrates the invention and uses an amphoteric rheological modifier of lamellar phases which monomeric composition is:

18.1 weight % of acrylic acid for the anionic charged monomer 59.8 weight % of acrylamide for the monomer with a nonionic character and 22.1 weight % of a cationic charged monomer of formula:

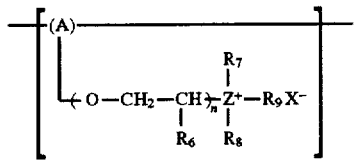

in which (A) is the methacrylate radical,

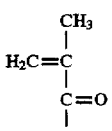

in the monomer and

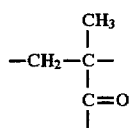

in the copolymer.

R6 is H
n=15−m
R$_7$ is CH$_3$
R$_8$ is —(A)—(O—CH$_2$—CH$_2$—)$_m$ with m+n=15
Z=N
R$_9$ is an alkyl radical with 12 carbon atoms
X=Cl
and which specific viscosity is 0.80.

The results of the measurement of the Brookfield viscosities for the different trials are grouped in Table 1 below, and show that for all the trials, the obtained compositions, according to the invention, are stable and homogenous.

TABLE 1

| | | RHEOLOGICAL MODIFIER | | | | DETERGENT FORMULATION | | | |
|---|---|---|---|---|---|---|---|---|---|
| | | MONOMER COMPOSITION | | | | MODIFIER | BROOKFIELD | | |
| | | ANIONIC | NONIONIC | CATIONIC | SPECIFIC | QUANTITY | VISCOSITY (mPa · s) | | |
| | TRIAL No. | (WEIGHT %) | (WEIGHT %) | (WEIGHT %) | VISCOSITY | (WEIGHT %) | 10 RPM | 20 RMP | 100 RPM |
| CONTROL | 1 | — | — | — | — | — | 5400 | 4600 | 3400 |
| INVENTION | 2 | 47.4 | 41.8 | 10.8 | 0.56 | 0.56 | 4800 | 4300 | 3300 |
| | 3 | 47.4 | 41.8 | 10.8 | 0.80 | 0.56 | 3900 | 1800 | 690 |
| | 4 | 47.4 | 41.8 | 10.8 | 2.03 | 0.56 | 2200 | 1500 | 620 |
| | 5 | 41.9 | 41.0 | 17.1 | 0.67 | 0.56 | 3000 | 1800 | 680 |
| | 6 | 36.6 | 40.2 | 23.2 | 0.56 | 0.56 | 1900 | 1100 | 370 |
| | 7 | 47.4 | 41.8 | 10.8 | 0.78 | 0.56 | 4500 | 2600 | 890 |
| | 8 | 89.2 | 0 | 10.8 | 0.46 | 0.56 | 1000 | 750 | 380 |
| | 9 | 18.1 | 59.8 | 22.1 | 0.80 | 0.56 | 1100 | 800 | 400 |

Reading Table 1 shows the fluidification, that is to say the decrease of the Brookfield viscosities at 10, 20 and 100 rpm of the anionic liquid detergent control composition when one uses, according to the invention, an amphoteric agent rheological modifier of lamellar phases of specific viscosity comprised between 0.3 and 3.0 and more specifically between 0.4 and 2.0.

Example 2

This example concerns the fluidification of a cationic liquid detergent composition by the use, according to the invention, of amphoteric rheological modifier of lamellar phases.

In order to achieve this goal, for each of the trials of the example, one prepares the cationic liquid detergent composition by adding into a 5 liter beaker, fitted with an agitator blade of 70 mm diameter, 1352 g of water and successively, 780 g of 9 times ethoxylated nonylphenol, 130 g of quaternary ammonium sold commercially by CECA under the name NORAMIUM M2SH1 and 338 g trisodium citrate.

The agitation is continued for 5 minutes before the required quantity of amphoteric agent corresponding to 0.56% dry weight of amphoteric agent based on the total weight of the formulation is added.

After 20 minutes of agitation of the composition thus obtained, one measures the viscosities of the different trials at 10, 20 and 100 rpm and 25° C. with a Brookfield viscometer of the RVT type equipped with the adequate spindle. The different trials are done with the following copolymer amphoteric rheological modifiers of lamellar phases:

Trial No. 10

This trial is the control in which no amphoteric agent rheological modifier of lamellar phases is introduced.

Trial No. 11

This trial illustrates the invention and uses the same amphoteric rheological modifier of lamellar phases as the one used in trial No. 3.

Trial No. 12

This trial illustrates the invention and uses the same amphoteric rheological modifier of lamellar phases as the one used in trial No. 4.

Trial No. 13

This trial illustrates the invention and uses an amphoteric rheological modifier of lamellar phases which monomeric composition is identical as the one used in trials No. 11 and No. 12 but which specific viscosity is 0.59.

Trial No. 14

This trial illustrates the invention and uses the same amphoteric rheological modifier of lamellar phases as the one used in trial No. 5.

Trial No. 15

This trial illustrates the invention and uses the same amphoteric rheological modifier of lamellar phases as the one used in trial No. 6.

Trial No. 16

This trial illustrates the invention and uses an amphoteric rheological modifier of lamellar phases which monomeric composition is:

26.4 weight % of acrylic acid for the anionic charged monomer 38.7 weight % of acrylamide for the monomer with nonionic character 10.0 weight % of cationic charged monomer of same formula as the one of trial No. 2 with cationic charge 24.9 weight % of trimethylaminoethyl methacrylate ammonium chloride as a second monomer with cationic charge, and which specific viscosity is 0.44.

Trial No. 17

This trial illustrates the invention and uses an amphoteric rheological modifier of lamellar phases which monomeric composition is:

15.4 weight % of acrylic acid for the anionic charged monomer 32.1 weight % of acrylamide for the monomer with nonionic character 8.3 weight % of cationic charged monomer of same formula as the one of trial No. 2 with cationic charge 44.2 weight % of trimethylaminoethyl methacrylate ammonium chloride as a second monomer with cationic charge, and which specific viscosity is 0.36.

Trial No. 18

This trial illustrates the invention and uses the same amphoteric rheological modifier of lamellar phases as the one used in trial No. 8.

Trial No. 19

This trial illustrates the invention and uses the same amphoteric rheological modifier of lamellar phases as the one used in trial No. 9.

The results of the measurements of the Brookfield viscosities for the different trials are grouped in Table 2 below, and show that for all the trials the obtained compositions, according to the invention, are stable and homogenous.

47.4 weight % of acrylic acid for the anionic charged monomer 41.8 weight % of acrylamide for the monomer with nonionic character

TABLE 2

| | | RHEOLOGICAL MODIFIER | | | | DETERGENT FORMULATION | | | |
|---|---|---|---|---|---|---|---|---|---|
| | | MONOMER COMPOSITION | | | | MODIFIER | BROOKFIELD | | |
| | | ANIONIC | NONIONIC | CATIONIC | SPECIFIC | QUANTITY | VISCOSITY (mPa · s) | | |
| | TRIAL No. | (WEIGHT %) | (WEIGHT %) | (WEIGHT %) | VISCOSITY | (WEIGHT %) | 10 RPM | 20 RMP | 100 RPM |
| CONTROL | 10 | — | — | — | — | — | 14400 | 6700 | 1440 |
| INVENTION | 11 | 47.4 | 41.8 | 10.8 | 0.80 | 0.56 | 140 | 140 | 125 |
| | 12 | 47.4 | 41.8 | 10.8 | 2.03 | 0.56 | 100 | 100 | 95 |
| | 13 | 47.4 | 41.8 | 10.8 | 0.59 | 0.56 | 560 | 460 | 182 |
| | 14 | 41.9 | 41.0 | 17.1 | 0.67 | 0.56 | 160 | 160 | 116 |
| | 15 | 36.6 | 40.2 | 23.2 | 0.56 | 0.56 | 1200 | 820 | 345 |
| | 16 | 26.4 | 38.7 | 34.9 | 0.44 | 0.56 | 1000 | 600 | 130 |
| | 17 | 15.4 | 32.1 | 52.5 | 0.36 | 0.56 | 1200 | 820 | 230 |
| | 18 | 89.2 | 0 | 10.8 | 0.46 | 0.56 | 1280 | 890 | 500 |
| | 19 | 18.1 | 59.8 | 22.1 | 0.80 | 0.56 | 110 | 104 | 104 |

Reading Table 2 shows the fluidification, that is to say the decrease of the Brookfield viscosities at 10, 20 and 100 rpm of the cationic liquid detergent control composition when one uses, according to the invention, an amphoteric rheological modifier of lamellar phases of specific viscosity comprised between 0.3 and 3.0 and more specifically between 0.4 and 2.0.

Example 3

This example concerns the thickening of an anionic liquid detergent composition by the use, according to the invention, of amphoteric rheological modifier of lamellar phases.

In order to achieve this goal, for each of the trials of the example, one prepares the anionic liquid detergent composition by adding into a 5 liter beaker, fitted with an agitator blade of 70 mm diameter, 361.3 g of water and 2.6 g of 100% sodium hydroxide. After complete dissolution of the sodium hydroxide, one adds under agitation 6.36 g of monoethanolamine, 63.6 g of sodium dodecylbenzene sulfonate and 152.1 g of 9 times ethoxylated nonylphenol respectively, before adding last and simultaneously 7.5 g sodium carbonate and 36.5 g trisodium citrate.

The agitation is continued for 5 minutes before the required quantity of amphoteric agent corresponding to 0.89% dry weight of amphoteric agent based on the total weight of the formulation is added.

After 20 minutes of agitation of the composition thus obtained, one measures the viscosities of the different trials at 10, 20 and 100 rpm and 25° C. with a Brookfield viscometer of the RVT type equipped with the adequate spindle. The different trials are done with the following amphoteric rheological modifiers of lamellar phases:

Trial No. 20

This trial is the control in which no amphoteric agent is introduced.

Trial No. 21

This trial illustrates the invention and uses an amphoteric rheological modifier of lamellar phases which monomeric composition is:

10.8 weight % of cationic charged monomer of same formula as the one of trial No. 2 with cationic charge and which specific viscosity is 7.9.

Trial No. 22

This trial illustrates the invention and uses an amphoteric rheological modifier of lamellar phases in a pulverized form which monomeric composition is:

49.2 weight % of acrylic acid for the anionic charged monomer 40.0 weight % of acrylamide for the monomer with nonionic character 10.8 weight % of cationic charged monomer of same formula as the one of trial No. 2 with cationic charge and which specific viscosity is greater than 10.

Trial No. 23

This trial illustrates the invention and uses an amphoteric rheological modifier of lamellar phases in a pulverized form which monomeric composition is:

29.3 weight % of acrylic acid for the anionic charged monomer 40.0 weight % of acrylamide for the monomer with nonionic character 30.7 weight % of cationic charged monomer of same formula as the one of trial No. 2 with cationic charge and which specific viscosity is greater than 10.

The results of the measurement of the Brookfield viscosities for the different trials are grouped in Table 3 below:

TABLE 3

| | TRIAL No. | RHEOLOGICAL MODIFIER | | | | DETERGENT FORMULATION | | | |
|---|---|---|---|---|---|---|---|---|---|
| | | MONOMER COMPOSITION | | | SPECIFIC VISCOSITY | MODIFIER QUANTITY (WEIGHT %) | BROOKFIELD VISCOSITY (mPa · s) | | |
| | | ANIONIC (WEIGHT %) | NONIONIC (WEIGHT %) | CATIONIC (WEIGHT %) | | | 10 RPM | 20 RMP | 100 RPM |
| CONTROL | 20 | — | — | — | — | — | 3300 | 2100 | 1970 |
| INVENTION | 21 | 47.4 | 41.8 | 10.8 | 7.90 | 0.89 | 6200 | 3500 | 2000 |
| | 22 | 49.2 | 40.0 | 10.8 | >10 | 0.89 | 30000 | 18750 | 5200 |
| | 23 | 29.3 | 40.0 | 30.7 | >10 | 0.89 | 26000 | 16750 | 4900 |

Reading Table 3 shows the thickening, that is to say the increase of the Brookfield viscosities at 10, 20 and 100 rpm of the anionic liquid detergent control composition when one uses, according to the invention, an amphoteric rheological modifier of lamellar phases of specific viscosity greater than 3 and more specifically greater than 10.

Example 4

This example concerns the thickening of a cationic liquid detergent composition by the use, according to the invention, of amphoteric agents rheological modifier of lamellar phases.

In order to achieve this goal, for each of the trials of the example, one prepares with the same procedure and the same material as the one used in example 2, the cationic liquid detergent composition composed of:

362.3 g of water 189 g of 9 times ethoxylated nonylphenol 31.5 g of quaternary ammonium sold commercially by CECA under the name NORAMIUM M2SH1 and 47.3 g of trisodium citrate.

Once the compositions are prepared, one adds in the same manner as for the example 2, and for each trial, 0.89 dry weight % of amphoteric agent based the total weight of the formulation, and after 20 minutes of agitation of the composition, one measures the Brookfield viscosities of the different trials at 10, 20 and 100 rpm and 25° C. using a Brookfield viscometer of the RVT type equipped with the adequate spindle.

The different trials are done with the following amphoteric rheological modifiers of lamellar phases:

Trial No. 24

This trial is the control in which no amphoteric agent is introduced.

Trial No. 25

This trial illustrates the invention and uses the same amphoteric rheological modifier of lamellar phases as the one used in trial No. 21.

Trial No. 26

This trial illustrates the invention and uses the same amphoteric rheological modifier of lamellar phases as the one used in trial No. 22.

Trial No. 27

This trial illustrates the invention and uses the same amphoteric rheological modifier of lamellar phases as the one used in trial No. 23.

The results of the measurements of the Brookfield viscosities for the different trials are grouped in Table 4 below:

TABLE 4

| | TRIAL No. | RHEOLOGICAL MODIFIER | | | | DETERGENT FORMULATION | | | |
|---|---|---|---|---|---|---|---|---|---|
| | | MONOMER COMPOSITION | | | SPECIFIC VISCOSITY | MODIFIER QUANTITY (WEIGHT %) | BROOKFIELD VISCOSITY (mPa · s) | | |
| | | ANIONIC (WEIGHT %) | NONIONIC (WEIGHT %) | CATIONIC (WEIGHT %) | | | 10 RPM | 20 RMP | 100 RPM |
| CONTROL | 24 | — | — | — | — | — | 400 | 350 | 300 |
| INVENTION | 25 | 47.4 | 41.8 | 10.8 | 7.9 | 0.89 | 7200 | 4400 | 1750 |
| | 26 | 49.2 | 40.0 | 10.8 | >10 | 0.89 | 16000 | 10500 | 3200 |
| | 27 | 29.3 | 40.0 | 30.7 | >10 | 0.89 | 20000 | 12000 | 3600 |

Reading Table 4 allows one to notice the thickening, that is to say the increase of the Brookfield viscosities at 10, 20 and 100 rpm of the cationic liquid detergent control composition when one uses, according to the invention, an amphoteric agent rheological modifier of lamellar phases of specific viscosity greater than 3 and more specifically greater than 10.

Example 5

This example concerns the fluidification of anionic cosmetic formulations of the shampoo type, by the use, according to the invention, of amphoteric rheological modifiers of lamellar phases in aqueous phases.

In order to achieve this goal, one tests the fluidification activity of an amphoteric rheological modifier of lamellar phases in aqueous phase for five different anionic liquid shampooing formulations.

Trial No. 28

This trial is a control and concerns the fabrication of a liquid shampoo in which no amphoteric agent has been added.

With this goal, and using the same procedure and material as in example 1, one prepares an anionic liquid shampooing composition having the following constituents:

105.1 g of water 0.8 g of 100% sodium hydroxide 2.42 g of monoethanolamine 24.2 g of sodium laurylethersulfate 70.2 g of 9 times ethoxylated nonylphenol 4.26 g of sodium carbonate 20 g of trisodium citrate.

After 20 minutes of agitation of the shampooing formulation thus prepared, one measures the Brookfield viscosities of the different trials at 10, 50 and 100 rpm and 25° C. using a Brookfield viscometer of the RVT type equipped with the adequate spindle.

Trial No. 29

This trial illustrates the invention and uses the same amphoteric rheological modifier of lamellar phases as the one used in trial No. 9. Thus, one adds, to the composition of trial No. 28, a quantity of the above-cited rheological modifier of lamellar phases corresponding to 0.56 dry weight % of the agent based on to the total weight of the formulation.

After 20 minutes of agitation of the composition thus prepared, one measures the viscosities of the different trials at 10, 50 and 100 rpm and 25° C. using a Brookfield viscometer of the RVT type equipped with the adequate spindle.

Trial No. 30

One makes a liquid shampooing control formulation using the same procedure and material as in trial No. 28, but having the following composition:

105.1 g of water 0.8 g of 100% sodium hydroxide 2.42 g of monoethanolamine 34.2 g of sodium laurylethersulfate 60.2 g of 9 times ethoxylated nonylphenol 4.26 g of sodium carbonate 20 g of trisodium citrate.

Trial No. 31

This trial illustrates the invention and uses the same amphoteric rheological modifier of lamellar phases as the one used in trial No. 9.

Thus, one adds, to the composition of trial No. 30, a quantity of the above-cited rheological modifier of lamellar phases corresponding to 0.56 dry weight % of the agent based on the total weight of the formulation.

After 20 minutes of agitation of the composition thus prepared, one measures the viscosities of the different trials at 10, 50 and 100 rpm and 25° C. using a Brookfield viscometer type RVT equipped with the adequate spindle.

Trial No. 32

One makes a third liquid shampooing control formulation using the same procedure and material as in trial No. 28, but having the following composition:

100 g of water 0.8 g of 100% sodium hydroxide 2.42 g of monoethanolamine 24.2 g of sodium laurylethersulfate 70.2 g of 9 times ethoxylated nonylphenol 5.33 g of sodium carbonate 25 g of trisodium citrate.

Trial No. 33

This trial illustrates the invention and uses the same amphoteric rheological modifier of lamellar phases as the one used in trial No. 9. Thus, one adds, to the composition of trial No. 32, a quantity of the above-cited rheological modifier of lamellar phases corresponding to 0.56 dry weight % of the agent based on the total weight of the formulation.

After 20 minutes of agitation of the composition thus prepared, one measures the viscosities of the different trials at 10 rpm, 50 rpm and 100 rpm and 25° C. using a Brookfield viscometer of the RVT type equipped with the adequate spindle.

Trial No. 34

One makes a fourth liquid shampooing control formulation using the same procedure and material as in trial No. 28, but having the following composition:

100 g of water 0.8 g of 100% sodium hydroxide 2.42 g of monoethanolamine 34.2 g of sodium laurylethersulfate 60.2 g of 9 times ethoxylated nonylphenol 5.33 g of sodium carbonate 25 g of trisodium citrate.

Trial No. 35

This trial illustrates the invention and uses the same amphoteric rheological modifier of lamellar phases as the one used in trial No. 9. Thus, one adds, to the composition of trial No. 34, a quantity of the above-cited rheological modifier of lamellar phases corresponding to 0.56 dry weight % of the agent based on the total weight of the formulation.

After 20 minutes of agitation of the composition thus prepared, one measures the viscosities of the different trials at 10 rpm, 50 rpm and 100 rpm and 25° C. using a Brookfield viscometer of the RVT type equipped with the adequate spindle.

Trial No. 36

One makes a fifth liquid shampooing control formulation using the same procedure and material as in trial No. 28, but having the following composition:

100 g of water 0.8 g of 100% sodium hydroxide 2.42 g of monoethanolamine 44.2 g of sodium laurylethersulfate 50.2 g of 9 times ethoxylated nonylphenol 5.33 g of sodium carbonate 25 g of trisodium citrate.

Trial No. 37

This trial illustrates the invention and uses the same amphoteric rheological modifier of lamellar phases as the one used in trial No. 9. Thus, one adds, to the composition of trial No. 36, a quantity of the above-cited rheological modifier of lamellar phases corresponding to 0.56 dry weight % of the agent based on the total weight of the formulation.

After 20 minutes of agitation of the composition thus prepared, one measures the viscosities of the different trials at 10 rpm, 50 rpm and 100 rpm and 25° C. using a Brookfield viscometer of the RVT type equipped with the adequate spindle.

The results of the measurements of the Brookfield viscosities for the different trials are grouped in Table 5 below, showing that for all the trials, the compositions obtained according to the invention, are stable and homogenous.

TABLE 5

| | TRIAL No. | RHEOLOGICAL MODIFIER | | | | COSMETIC FORMULATION | | | |
| --- | --- | --- | --- | --- | --- | --- | --- | --- | --- |
| | | MONOMER COMPOSITION | | | | MODIFIER QUANTITY (WEIGHT %) | BROOKFIELD VISCOSITY (mPa · s) | | |
| | | ANIONIC (WEIGHT %) | NONIONIC (WEIGHT %) | CATIONIC (WEIGHT %) | SPECIFIC VISCOSITY | | 10 RPM | 50 RMP | 100 RPM |
| CONTROL | 28 | — | — | — | — | — | 22000 | 2700 | 600 |
| INVENTION | 29 | 18.1 | 59.8 | 22.1 | 0.80 | 0.56 | 220 | 168 | 156 |
| CONTROL | 30 | — | — | — | — | — | 2800 | 760 | 420 |
| INVENTION | 31 | 18.1 | 59.8 | 22.1 | 0.80 | 0.56 | 80 | 80 | 80 |
| CONTROL | 32 | — | — | — | — | — | IMPOSSIBLE MEASUREMENT | 8000 | 5000 |
| INVENTION | 33 | 18.1 | 59.8 | 22.1 | 0.80 | 0.56 | 160 | 160 | 160 |
| CONTROL | 34 | — | — | — | — | — | 53000 | 6900 | 1500 |
| INVENTION | 35 | 18.1 | 59.8 | 22.1 | 0.80 | 0.56 | 130 | 130 | 128 |
| CONTROL | 36 | — | — | — | — | — | 1500 | 640 | 420 |
| INVENTION | 37 | 18.1 | 59.8 | 22.1 | 0.80 | 0.56 | 85 | 85 | 85 |

Reading Table 5 shows the fluidification, that is to say the decrease of the Brookfield viscosities at 10 rpm, 50 rpm and 100 rpm of the anionic liquid cosmetic control composition when one uses, according to the invention, an amphoteric agent rheological modifier of lamellar phases of specific viscosity comprised between 0.3 and 3.0.

Example 6

This example concerns the thickening of cosmetic compositions, by the use, according to the invention, of amphoteric rheological modifiers of lamellar phases in aqueous phases.

In order to achieve this goal, one tests the efficacy of an amphoteric rheological modifier of lamellar phases in aqueous phase for an anionic liquid shampooing formulations as well as for a cationic liquid shampooing formulation.

Trial No. 38

This trial is a control and concerns the fabrication of an anionic liquid shampoo in which no amphoteric agent rheological modifier of lamellar phases has been added.

With this goal, and using the same procedure and material as in example 1, one prepares an anionic liquid shampooing composition having the following constituents:

325.2 g of water
1.6 g of 100% sodium hydroxide
4.84 g of monoethanolamine
68.4 g of sodium laurylethersulfate
120.4 g of 9 times ethoxylated nonylphenol
8.52 g of sodium carbonate
40 g of trisodium citrate.

After 20 minutes of agitation of the shampooing formulation thus prepared, one measures the Brookfield viscosities of the different trials at 10, 20 and 100 rpm and 25° C. using a Brookfield viscometer of the RVT type equipped with the adequate spindle.

It is to be noted that after resting for several minutes, the formulation decants thus creating two phases.

Trial No. 39

This trial illustrates the invention and uses the same amphoteric agent as the one used in trial No. 22.

Thus, one adds, to the composition of trial No. 38, a quantity of the above-cited rheological modifier of lamellar phases corresponding to 0.89 dry weight % of the agent based on the total weight of the formulation.

After 20 minutes of agitation of the composition thus prepared, one measures the viscosities of the different trials at 10, 20 and 100 rpm and 25° C. using a Brookfield viscometer of the RVT type equipped with the adequate spindle.

Trial No. 40

This example is a control trial concerning the fabrication of a cationic liquid shampooing formulation without addition of an amphoteric agent rheological modifier of lamellar phases.

In order to achieve this goal, one prepares with the same procedure and the same material as the one used in example 2, the cationic liquid shampooing composition by successive addition of:

201 g of water
105 g of 9 times ethoxylated nonylphenol
17.5 g of NORAMIUM M2SH1 and
26.3 g of trisodium citrate.

After 20 minutes of agitation, the Brookfield viscosities of the different trials at 10 rpm, 20 rpm and 100 rpm and 25° C. are measured using a Brookfield viscometer of the RVT type equipped with the adequate spindle.

Trial No. 41

This trial illustrates the invention and uses the same amphoteric rheological modifier of lamellar phases as the one used in trial No. 22.

Thus, one adds to the composition of trial No. 40, a quantity of the above-cited rheological modifier of lamellar phases corresponding to 0.89 dry weight % of the agent based on the total weight of the formulation and after 20 minutes of agitation, one proceeds, as previously, to the measurement of the different Brookfield viscosities.

The results of the measurements of the Brookfield viscosities for the different trials are grouped in Table 6 below:

TABLE 6

| | TRIAL No. | RHEOLOGICAL MODIFIER | | | | COSMETIC FORMULATION | | | |
|---|---|---|---|---|---|---|---|---|---|
| | | MONOMER COMPOSITION | | | | MODIFIER | BROOKFIELD | | |
| | | ANIONIC | NONIONIC | CATIONIC | SPECIFIC | QUANTITY | VISCOSITY (mPa · s) | | |
| | | (WEIGHT %) | (WEIGHT %) | (WEIGHT %) | VISCOSITY | (WEIGHT %) | 10 RPM | 20 RMP | 100 RPM |
| CONTROL | 38 | — | — | — | — | — | 900 | 500 | 180 |
| INVENTION | 39 | 49.2 | 40.0 | 10.8 | >10 | 0.89 | 3600 | 1400 | 740 |
| CONTROL | 40 | — | — | — | — | — | 3800 | 2050 | 910 |
| INVENTION | 41 | 49.2 | 40.0 | 10.8 | >10 | 0.89 | 21200 | 12000 | 3480 |

Reading Table 6 shows the thickening, that is to say the increase of the Brookfield viscosities at 10, 20 and 100 rpm of the cationic liquid shampooing control composition or anionic control when one uses, according to the invention, an amphoteric rheological modifier of lamellar phases of specific viscosity greater than 3 and preferably greater than 10.

Example 7

This example concerns the obtention of liquid detergent compositions comprising simultaneously an anionic lamellar phase and a cationic lamellar phase as well as the compatibility of the phases thus obtained using amphoteric rheological modifiers of lamellar phases in aqueous phase.

With this goal, and using the same procedure and material as in example 1, one prepares an anionic liquid detergent composition having the following constituents:

132 g of water 0.98 g of 100% sodium hydroxide 2.42 g of monoethanolamine 24.2 g of dodecylbenzene sodium sulfonate 65.45 g of 9 times ethoxylated nonylphenol 2.87 g of sodium carbonate 13.57 g of trisodium citrate.

In the same way this anionic formulation is made, one prepares, using the same procedure and material as in example 2, the cationic composition of example 2 which could correspond to a fabric softener used in detergents.

Those two lamellar phases of opposite ionicity being made, one proceeds, on one hand, to the simple mixing of the two phases in different proportions before the measurements, when possible, of the Brookfield viscosities are done, using the same procedures and material as for the previous trials, and on the other hand to the simultaneous mixing of the two phases of opposed ionicity in the same proportions as before with the amphoteric rheological modifier of lamellar phases of trial No. 9, using a quantity equivalent to 0.56 dry weight % of the agent based on the total weight of the mixture, before the rheological behavior is determined by the measurement of the Brookfield viscosities at 10 rpm, 50 rpm and 100 rpm using the same procedure and material as for the previous trials and after having observed the stability and homogeneity of the obtained mixtures according to the invention.

The different proportions tested are for trial No. 42:

84.4 weight % of anionic phase 15.6 weight % of cationic phase for trial No. 43:

50 weight % of anionic phase 50 weight % of cationic phase for trial No. 44:

15.7 weight % of anionic phase 84.3 weight % of cationic phase

The results of the measurements of the Brookfield viscosities for the different trials are gathered in Table 7 below:

TABLE 7

| | | TRIAL No. | | |
|---|---|---|---|---|
| | | 42 | 43 | 44 |
| COMPOSITION | % ANIONIC | 84.4 | 50 | 15.7 |
| | % CATIONIC | 15.6 | 50 | 84.3 |
| BROOKFIELD VISCOSITY (mPa · s) | | | | |
| CONTROL (0% AGENT) | 10 RPM | IMPOSSIBLE MEASUREMENT | 2400 | RAPID SET-TLING |
| | 50 RPM | IMPOSSIBLE MEASUREMENT | 760 | |
| | 100 RPM | IMPOSSIBLE MEASUREMENT | 540 | |
| INVENTION (0.56% AGENT) | 10 RPM | 520 | 140 | 104 |
| | 50 RPM | 200 | 110 | 104 |
| | 100 RPM | 160 | 110 | 104 |

Reading Table 7 shows that one obtains a mixture that is, at the same time, fluid that is to say presenting a weak Brookfield viscosity, stable and homogenous that is to say without rapid settling, when an amphoteric rheological modifier of lamellar phases in aqueous phases is used according to the invention.

Example 8

This example concerns the obtention of liquid cosmetic compositions comprising simultaneously an anionic lamellar phase and a cationic lamellar phase as well as the compatibility of the phases thus obtained using amphoteric rheological modifiers of lamellar phases in aqueous phase.

With this goal, and using the same procedure and material as in trial No. 38, one prepares a liquid anionic shampooing composition having the same composition as the one used in trial No. 38.

In the same way this anionic formulation is made, one prepares, using the same procedure and material as in trial No. 40, the cationic composition used in trial No. 40.

Those two lamellar phases of opposite ionicity being made, one proceeds, on one hand, to the simple mixing of the two phases in different proportions before the measurements, when possible, of the Brookfield viscosities at 10 rpm, 20 rpm and 100 rpm are done, using the same procedures and material as for the previous trials, and on the other hand to the simultaneous mixing of the two phases of opposite ionicity in the same proportions as before with the amphoteric rheological modifier of lamellar phases of trial No. 22, using the equivalent of 0.89 dry weight % of the agent based on the total weight of the mixture, before the rheological behavior is determined by the measurement of the Brookfield viscosities using the same procedure and material as for the previous trials.

The different proportions tested are for trial No. 45:
66.7 weight % of anionic phase
33.3 weight % of cationic phase
for trial No. 46:
50 weight % of anionic phase
50 weight % of cationic phase
for trial No. 47:
33.3 weight % of anionic phase
66.7 weight % of cationic phase The results of the measurements of the Brookfield viscosities for the different trials are gathered in Table 8 below:

TABLE 8

|  |  | TRIAL No. | | |
|---|---|---|---|---|
|  |  | 45 | 46 | 47 |
| COMPOSITION | % ANIONIC | 66.7 | 50 | 33.3 |
|  | % CATIONIC | 33.3 | 50 | 66.7 |
| BROOKFIELD VISCOSITY (mPa · s) |  |  |  |  |
| CONTROL (0% AGENT) | 10 RPM | RAPID SETTLING | RAPID SETTLING | 56500 |
|  | 20 RPM | RAPID SETTLING | RAPID SETTLING | 20000 |
|  | 100 RPM | RAPID SETTLING | RAPID SETTLING | 2400 |
| INVENTION (0.89% AGENT) | 10 RPM | 28000 | 22400 | 66000 |
|  | 20 RPM | 17800 | 13000 | 39000 |
|  | 100 RPM | 3200 | 4600 | 10800 |

Reading Table 8 shows that the obtained mixture is stable and homogenous, that is to say without rapid settling, when an amphoteric rheological modifier of lamellar phases in aqueous phases is used according to the invention.

Example 9

This example concerns the determination of the minimal quantity of amphoteric agent needed in the detergent or cosmetic composition to effectively modify the rheology of the lamellar phases in aqueous phase.

With this goal, using the liquid control cationic detergent composition of trial No. 10, it is implemented, with the same procedure and material as the one used in example 2, a quantity of the amphoteric agent corresponding to 0.15 dry weight % of the amphoteric agent used in trial No. 9 based on the total weight of the formulation for the trial No. 48 and corresponding to 0.45 dry weight % of the same amphoteric agent based on the total weight of the formulation for the trial No. 49.

In the same way, using the liquid control anionic detergent composition of trial No. 20, it is implemented, with the same procedure and material as the one used in example 3, a quantity of amphoteric agent corresponding to 0.15 dry weight % of the amphoteric agent used in trial No. 22 based on the total weight of the formulation for the trial No. 50 and corresponding to 0.30 dry weight % of the same amphoteric agent based on the total weight of the formulation for the trial No. 51.

The measurements of the Brookfield viscosities of the compositions of the different trials thus obtained, are carried out in the same conditions and with the same materials as for the previous trials. The results of the different measurements are gathered in Table 9 below:

TABLE 9

|  |  | RHEOLOGICAL MODIFIER | | | | DETERGENT FORMULATION | | | |
|---|---|---|---|---|---|---|---|---|---|
|  |  | MONOMER COMPOSITION | | | | MODIFIER | BROOKFIELD | | |
|  |  | ANIONIC | NONIONIC | CATIONIC | SPECIFIC | QUANTITY | VISCOSITY (mPa · s) | | |
|  | TRIAL No. | (WEIGHT %) | (WEIGHT %) | (WEIGHT %) | VISCOSITY | (WEIGHT %) | 10 RPM | 20 RMP | 100 RPM |
| CONTROL | 10 | — | — | — | — | — | 14400 | 6700 | 1440 |
|  | 48 | 18.1 | 59.8 | 22.1 | 0.80 | 0.15 | SETTLING | SETTLING | SETTLING |
| INVENTION | 49 | 18.1 | 59.8 | 22.1 | 0.80 | 0.45 | 400 | 350 | 215 |
| CONTROL | 20 | — | — | — | — | — | 3300 | 2100 | 1970 |
|  | 50 | 49.2 | 40.0 | 10.8 | >10 | 0.15 | 9600 | 6700 | 1900 |
| INVENTION | 51 | 49.2 | 40 | 10.8 | >10 | 0.3 | 26000 | 9300 | 6150 |

Reading Table 9 shows that a stable and homogenous mixture is obtained when at least 0.25 dry weight % based on the total weight of the composition of an amphoteric rheological modifier of lamellar phases in aqueous phase is used according to the invention.

This application is based on French Patent Application No. 95 03646 filed on Mar. 23, 1995, and which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A method for modifying the rheological properties of a detergent or cosmetic composition containing a lamellar phase, said method comprising adding to said composition an amphoteric copolymer comprising at least a first type of monomeric unit being derived from one or more ethylenically unsaturated monomers having an anionic charge, said second type of monomeric unit being derived from one or more ethylenically unsaturated monomers having a cationic charge, with one at least of said cationic charged monomers having a surface-active structure, and optionally comprising a third type of monomeric unit derived from one or more ethylenically unsaturated nonionic monomers, and wherein said copolymer has the formula (I):

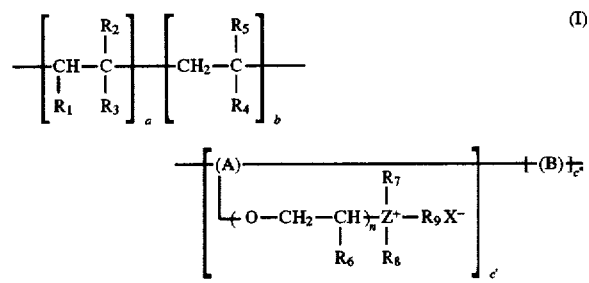

in which:

$R_1$ is H or COOH, $R_2$ is H or $CH_3$, $R_3$ is a group having at least an acidic function which may be totally or partially neutralized, and a is a number such that the weight percentage of the anionic monomeric unit, based on the total weight of all monomers is, limits included, between 95 and 15;

$R_4$ is

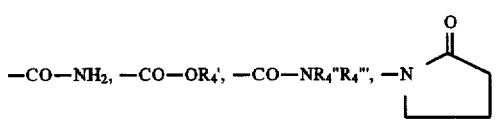

in which $R_4'$ is an alkyl or alkoxy radical having 1 to 4 carbon atoms, $R_4''$ is H or alkyl radical having 1 to 4 carbon atoms, $R_4'''$ is an alkyl radical having 1 to 4 carbon atoms, $R_5$ is H or $CH_3$, and b is a number such that the weight percentage of the nonionic monomeric unit, based on the total weight of all monomers is, limits included, between 0 and 65;

A is a monomeric unit derived from a polymerizable unsaturated radical selected from the group consisting of acrylic, methacrylic, maleic, itaconic, crotonic, and vinylphthalic esters, maleic, itaconic, vinylphthalic hemiesters, acrylurethane, methacrylurethane, α,α-dimethyl-m-isopropenyl benzylurethane, allylurethane, allylic ethers, substituted or unsubstituted acrylamides, substituted or unsubstituted methacrylamides, and vinyl groups;

$R_6$ is H or $CH_3$, n=2 to 30, $R_7$ is an alkyl group having 1 to 4 carbon atoms, Z is N or S, X is a sulfate or halogen counter-ion and when Z is N:

$R_8$ is an alkyl chain having 8 to 22 carbon atoms or a linking group to another polymeric chain of formula (I) having the following formula:

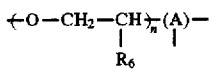

with n=2 to 30, where A has the same meaning as above and the two bonds from A are connected to two monomer units in another polymer chain of formula (I), and $R_9$ is an alkyl chain having 8 to 22 carbon atoms and when Z is S:

$R_8$ does not exist $R_9$ is an alkyl chain having 8 to 22 carbon atoms, and c' is a number such that the weight percentage, based on the total weight of all monomers, of the cationic charged monomer having a surface-active structure, is, limits included, between 5 and 60 with c'+c''=c; c representing the weight percentage of all cationic monomers and varying between 5 and 60, limits included; and B is a cationic monomeric unit, c'' is a number such that the weight percentage, based on the total weight of all monomers, of the cationic monomer which does not contain a surface-active structure is, limits included, between 0 and 55.

2. The method of claim 1 wherein said detergent or cosmetic compositions are liquid or pasty.

3. The method of claim 1 wherein said lamellar phase of said cosmetic or detergent composition is an anionic lamellar phase, a cationic lamellar phase, or a mixture of an anionic lamellar phase and a cationic lamellar phase.

4. The method of claim 1, wherein said rheological modification is a fluidification of a detergent or cosmetic composition wherein a is, limits included, between 80 and 25;

b is, limits included, between 20 and 50;

B is selected from the group consisting of trimethylaminoethyl acrylate chloride, trimethylaminoethyl methacrylate chloride, trimethylaminoethyl acrylate sulfate, trimethylaminoethyl methacrylate sulfate, trimethylaminopropyl acrylamide chloride, trimethylaminopropyl methacrylamide chloride, trimethylaminopropyl acrylamide sulfate, and trimethylaminopropyl methacrylamide sulfate, and said copolymer has a specific viscosity between 0.3 and 3.0.

5. The method of claim 4, wherein said specific viscosity is between 0.4 and 2.0.

6. The method of claim 4, wherein c' is, limits included, between 10 and 35, and c is, limits included, between 10 and 35.

7. The method of claim 4, wherein C'' is, limits included, between 1 and 55.

8. The method of claim 1, wherein said rheological modification is a thickening of a detergent or cosmetic composition and wherein B is a cationic monomeric unit derived from a monomer selected from the group consisting of trimethylaminoethyl acrylate chloride, trimethylaminoethyl methacrylate chloride, trimethylaminoethyl acrylate sulfate, trimethylaminoethyl methacrylate sulfate, trimethylaminopropyl acrylamide chloride, trimethylaminopropyl methacrylamide chloride, trimethylaminopropyl acrylamide sulfate, and trimethylaminopropyl methacrylamide sulfate, and said copolymer has a specific viscosity greater than 3.0.

9. The method of claim 8, wherein said specific viscosity is greater than 10.

10. The method of claim 8, wherein c' is, limits included, between 10 and 35, and c is, limits included, between 10 and 35.

11. The method of claim 8, wherein C" is, limits included, between 1 and 55.

12. The method of claim 1, wherein said rheological modification is an improvement of compatibility of a detergent or cosmetic composition containing a mixture of anionic and cationic lamellar phases and wherein B is a cationic monomeric unit derived from a monomer selected from the group consisting of trimethylaminoethyl acrylate chloride, trimethylaminoethyl methacrylate chloride, trimethylaminoethyl acrylate sulfate, trimethylaminoethyl methacrylate sulfate, trimethylaminopropyl acrylamide chloride, trimethylaminopropyl methacrylamide chloride, trimethylaminopropyl acrylamide sulfate, and trimethylaminopropyl methacrylamide sulfate.

13. The method of claim 12, wherein c' is, limits included, between 10 and 35, and c is, limits included, between 10 and 35.

14. The method of claim 12, wherein C" is, limits included, between 1 and 55.

15. The method of claim 1, wherein at least 0.25 dry weight % of said copolymer based on the total weight of said detergent or cosmetic composition is added.

16. A liquid detergent composition, comprising at least 0.2 dry wt. %, based on the total weight of the composition, a rheological modifier, which is an amphoteric copolymer comprising at least a first and a second type of monomeric units with said first type of monomeric unit being derived from one or more ethylenically unsaturated monomers having an anionic charge, said second type of monomeric unit being derived from one or more ethylenically unsaturated monomers having a cationic charge, with one at least of said cationic charged monomers having a surface-active structure, and optionally comprising a third type of monomeric unit derived from one or more ethylenically unsaturated nonionic monomers, and wherein said copolymer has the formula (I):

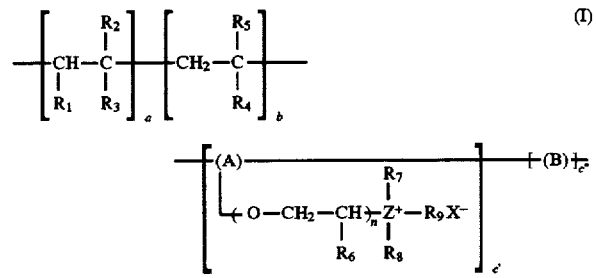

in which:

$R_1$ is H or COOH, $R_2$ is H or $CH_3$, $R_3$ is a group having at least an acidic function which may be totally or partially neutralized, and a is a number such that the weight percentage of the anionic monomeric unit, based on the total weight of all monomers is, limits included, between 95 and 15;

$R_4$ is $-CO-NH_2, -CO-OR_4', -CO-NR_4''R_4''', -N$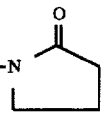

in which $R_4'$ is an alkyl or alkoxy radical having 1 to 4 carbon atoms, $R_4''$ is H or alkyl radical having 1 to 4 carbon atom, $R_4'''$ is an alkyl radical having 1 to 4 carbon atoms, $R_5$ is H or $CH_3$, and b is a number such that the weight percentage of the nonionic monomeric unit, based on the total weight of all monomers is, limits included, between 0 and 65;

A is a monomeric unit derived from a polymerizable unsaturated radical selected from the group consisting of acrylic, methacrylic, maleic, itaconic, crotonic, and vinylphthalic esters, maleic, itaconic, vinylphthalic hemiesters, acrylurethane, methacrylurethane, α, α-dimethyl-m-isopropenyl benzylurethane, allylurethane, allylic ethers, substituted or unsubstituted acrylamides, substituted or unsubstituted methacrylamides, and vinyl groups;

$R_6$ is H or $CH_3$, n=2 to 30, $R_7$ is an alkyl group having 1 to 4 carbon atoms, Z is N or S, X is a sulfate or halogen counter-ion and when Z is N:

$R_8$ is an alkyl chain having 8 to 22 carbon atoms or a linking group to another polymeric chain of formula (I) having the following formula:

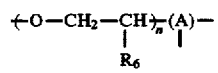

with n=2 to 30, where A has the same meaning as above and the two bonds from A are connected to two monomer units in another polymeric chain of formula (I), and $R_9$ is an alkyl chain having 8 to 22 carbon atoms and when Z is S:

$R_8$ does not exist $R_9$ is an alkyl chain having 8 to 22 carbon atoms, and c' is a number such that the weight percentage, based on the total weight of all monomers, of the cationic charged monomer having a surface-active structure is, limits included, between 5 and 60, with c'+c"=c; c representing the weight percentage of all cationic monomers and varying between 5 and 60, limits included; and B is a cationic monomeric unit, c" is a number such that the weight percentage, based on the total weight of all monomers, of the cationic monomer which does not contain a surface-active structure is, limits included, between 0 and 55.

17. The liquid detergent of claim 16, which is a liquid washing detergent.

18. A liquid or pasty cosmetic composition, comprising at least 0.2 dry wt. %, based on the total weight of the composition, a rheological modifier, which is an amphoteric copolymer comprising at least a first and a second type of monomeric units with said first type of monomeric unit being derived from one or more ethylenically unsaturated monomers having an anionic charge, said second type of monomeric unit being derived from one or more ethylenically unsaturated monomers having a cationic charge, with one at least of said cationic charged monomers having a surface-active structure, and optionally comprising a third type of monomeric unit derived from one or more ethylenically unsaturated nonionic monomers, and wherein said copolymer has the formula (I):

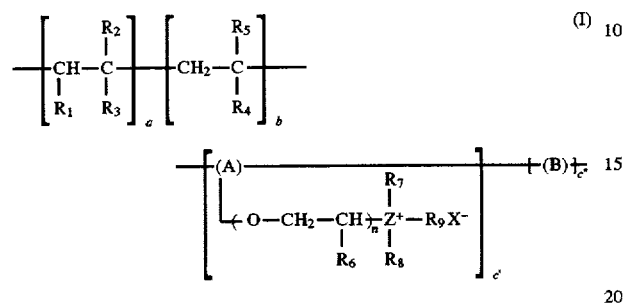

in which:

$R_1$ is H or COOH, $R_2$ is H or $CH_3$, $R_3$ is a group having at least an acidic function which may be totally or partially neutralized, and a is a number such that the weight percentage of the anionic monomeric unit, based on the total weight of all monomers is, limits included, between 95 and 15;

$R_4$ is

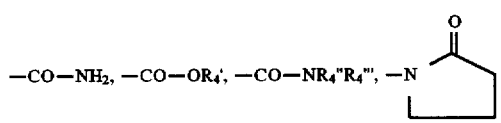

in which $R_4'$ is an alkyl or alkoxy radical having 1 to 4 carbon atoms, $R_4''$ is H or alkyl radical having 1 to 4 carbon atoms, $R_4'''$ is an alkyl radical having 1 to 4 carbon atoms, $R_5$ is H or $CH_3$, and b is a number such that the weight percentage of the nonionic monomeric unit, based on the total weight of all monomers is, limits included, between 0 and 65;

A is a monomeric unit derived from a polymerizable unsaturated radical selected from the group consisting of acrylic, methacrylic, maleic, itaconic, crotonic, and vinylphthalic esters, maleic, itaconic, vinylphthalic hemiesters, acrylurethane, methacrylurethane, α, α-dimethyl-m-isopropenyl benzylurethane, allylurethane, allylic ethers, substituted or unsubstituted acrylamides, substituted or unsubstituted methacrylamides, and vinyl groups;

$R_6$ is H or $CH_3$, n=2 to 30, $R_7$ is an alkyl group having 1 to 4 carbon atoms, Z is N or S, X is a sulfate or halogen counter-ion and when Z is N:

$R_8$ is an alkyl chain having 8 to 22 carbon atoms or a linking group to another polymeric chain of formula (I) having the following formula:

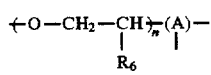

with n=2 to 30, where A has the same meaning as above and the two bonds from A are connected to two monomer units in another polymeric chain of formula (I), and $R_9$ is an alkyl chain having 8 to 22 carbon atoms and when Z is S:

$R_8$ does not exist $R_9$ is an alkyl chain having 8 to 22 carbon atoms, and c' is a number such that the weight percentage, based on the total weight of all monomers, of the cationic charged monomer having a surface-active structure is, limits included, between 5 and 60, with c'+c''=c; c representing the weight percentage of all cationic monomers and varying between 5 and 60, limits included; and B is a cationic monomeric unit, c'' is a number such that the weight percentage, based on the total weight of all monomers, of the cationic monomer which does not contain a surface-active structure is, limits included, between 0 and 55.

19. The cosmetic composition of claim 18, which is a shampoo.

* * * * *